United States Patent [19]
Busch

[11] 3,961,634
[45] June 8, 1976

[54] HAIR BLEACHING PREPARATIONS CONTAINING KERATOSE AND PROCESSES OF USING THE SAME

[75] Inventor: Peter Busch, Willich, Germany

[73] Assignee: Henkel & Cie G.m.b.H., Dusseldorf, Germany

[22] Filed: July 23, 1974

[21] Appl. No.: 491,050

[30] Foreign Application Priority Data
July 30, 1973  Germany............................ 2338518

[52] U.S. Cl. ....................... 132/7; 8/10.2; 260/123.7; 424/DIG. 2; 424/DIG. 3; 424/62; 424/70; 424/71; 424/359
[51] Int. Cl.² ...................... A45D 7/04; A61K 7/135
[58] Field of Search ............... 424/62, 70, 71, 359, 424/DIG. 2, DIG. 3; 132/7; 260/123.7

[56] References Cited
UNITED STATES PATENTS

| 2,413,983 | 1/1947 | Lustig et al. ................... 260/112 |
| 2,434,688 | 1/1948 | Evans ............................ 8/127.6 X |
| 2,474,339 | 6/1949 | Ward et al. ...................... 252/316 |
| 2,540,494 | 2/1951 | Schwarz ......................... 424/72 X |
| 3,378,444 | 4/1968 | Swanson ......................... 424/62 |
| 3,542,918 | 11/1970 | Berth et al. ..................... 424/62 |
| 3,683,939 | 8/1972 | Johnsen et al. ................. 424/62 X |

OTHER PUBLICATIONS

Neurath, The Proteins, vol. IV, Academic Press, New York, (1966), pp. 316–318.

Primary Examiner—Sam Rosen
Assistant Examiner—Vera C. Clarke
Attorney, Agent, or Firm—Hammond & Littell

[57] ABSTRACT

Process and composition for bleaching hair containing oxidizing agents which liberate active oxygen, and which contain keratose so as to reduce damage to the hair.

9 Claims, No Drawings

HAIR BLEACHING PREPARATIONS CONTAINING KERATOSE AND PROCESSES OF USING THE SAME

THE PRIOR ART

Compounds liberating active oxygen, or oxidizing agents, have long been utilized in bleaching and coloring hair with oxidation dyestuffs coloring agents. The main examples of such oxidizing agents are hydrogen peroxide or percarbamide, alkali metal perborate, such as sodium perborate, melamine perhydrate, or alkali metal percarbonates, optionally with alkali metal persulfate addition. However, this oxidative treatment of the hair not only bleaches the hair pigment, but also is injurious to the fibrous material of the hair. Evidence of this damage can be found in the numerous physical and chemical alterations in the hair, of which the most conspicuous are impairment of texture and shine of the hair, increased brittleness, especially breaking of the hair ends, reduction in resistance to splitting and increased alkali solubility of the hair.

OBJECTS OF THE INVENTION

It is an object of the present invention to provide a composition for bleaching and coloring hair which contains keratose and oxidizing agents which liberate active oxygen, and to provide a process for using this composition.

It is another object of the present invention to provide a composition and method for bleaching and coloring hair which do not cause any substantial damage to the fibrous material of the hair.

These and further objects of the present invention will become apparent as the description thereof proceeds.

DESCRIPTION OF THE INVENTION

This invention relates to agents or compositions for bleaching and coloring hair based on compounds which liberate active oxygen, and which contain keratose so as to reduce damage to the hair, as well as relating to a process for utilizing these agents to bleach and color hair.

More particularly the present invention provides a preparation for the bleaching and coloring of hair consisting essentially of A. from 0.05% to 10% by weight of keratose,
B. from 3% to 10% by weight of at least one oxidizing agent for liberating active oxygen, but calculated as pure hydrogen peroxide, and
C. the balance at least one ingredient selected from the group consisting of a wetting agent, a thickening agent, a direct dye, an oxidation dyestuffs combination of a coupler and a developer, an oil replacement agent, a perfume, a pH adjustment reagent, water and the mixtures thereof.

The present invention is, in addition, directed to an improvement in the process for bleaching and coloring hair which comprises applying a bleaching and coloring agent containing an oxidizing agent to the hair at a temperature and for a time effective to bleach and to color said hair, and removing said agent from the hair. The improvement consists essentially in the presence of from 0.05% to 10% by weight of keratose in said bleaching and coloring agent containing an oxidizing agent.

The present invention furthermore relates to a process for the bleaching and coloring of human hair consisting essentially of applying to said hair at a temperature ranging from about 15°C to 40°C for a time sufficient to bleach and to color said hair, an effective amount of a preparation consisting essentially of A. from 0.05% to 10% by weight of keratose based upon the total weight,
B. from 3% to 10% by weight of at least one oxidizing agent for liberating active oxygen, based upon the total weight but calculated as pure hydrogen peroxide, and
C. the balance up to 100% by weight of at least one ingredient selected from the group consisting of a wetting agent, a thickening agent, a direct dye, an oxidation dyestuffs combination of a coupler and a developer, an oil replacement agent, a perfume, a pH adjustment reagent, water and the mixtures thereof.

The present invention has the advantages that agents for bleaching and coloring hair, based on compounds which liberate active oxygen and contain keratose, do not cause any substantial damage to the fibrous material of the hair. Hair which is treated with agents containing compounds liberating active oxygen and containing added keratose, has a more glossy appearance, is less matted and is softer to the touch than hair which had been treated in the previously known manner without the addition of keratose. Physical and chemical tests convincingly verify that utilization of the agents of the invention affords protective treatment of the hair.

Keratose is a hydrolytic product of keratin.

The keratose added to the compositions of the invention, as a component for reducing damage to the hair, chemically comprises an oxidized keratin. Keratose can be prepared in a known manner by means of oxidative alkaline treatment of material containing keratin such as hair, nails, claws, hooves and feathers. To this end, after the oil has been removed from the keratin material and after oxidation has been effected, said materials are treated at an increased temperature in the alkaline medium with aqueous bases, and the keratose solutions thus prepared are then dehydrated. The resulting keratose is a syrupy substances which varies in color.

The compositions according to this invention containing keratose and oxidizing agents which liberate active oxygen, may be utilized as a preparation in the form of a solution, a gel, a cream or a powder. The amount of keratose ranges from 0.05% to 10% by weight, preferably from 3% to 7% by weight, based on the total weight of the preparation.

Suitable examples of oxidizing agents which liberate active oxygen include, for example, hydrogen peroxide, precarbamide or alkali metal salts of perborate or percarbonate, such as the sodium salt, melamine perhydrate, optionally with alkali metal persulfate addition in known quantities employed in customary preparations. In this case hydrogen peroxide, which is added in the form of an approximately 3% to 10% solution, has special practical significance. The oxidizing agent portion of the composition of the invention may consists of one or more of such per-compounds. The amount of the oxidizing agent is based upon the total weight and may vary from 3% to 10%, when calculated as pure hydrogen peroxide.

In compositions of this type for bleaching and coloring hair, the agents of the invention can contain the additive ingredients usually present in such preparations, such as thickeners, oil replacement agents, wetting agents, coloring agents and perfumes.

Most suitable for use as thickeners are cellulose derivatives, for example methyl cellulose, polyvinyl pyrrolidone, polyacrylates such as poly-lower alkyl acrylates and methacrylates, alkali metal alginates, as well as higher fatty alcohols together with the rest or alone. The fatty alcohols have at the same time oil replacement properties. Suitable wetting agents include the anionic and nonionic surface-active compounds such as, for example, higher fatty alcohol-sulfates, higher fatty alcohol lower alkylene oxide adducts-sulfates, condensation products of higher fatty alcohols with ethylene oxide, and alkyl-benzene sulfonates.

In the case of the coloring agents which may, in certain cases, be added, oxidation dyestuffs combination of a developer component and a coupler component can be used, or direct dyeing dyestuffs, if the latter are added to effect a bleaching and coloring.

The various ingredients are utilized in the amounts effective for this purpose. An effective amount of a wetting agent or surfactant added is especially from 0.5% to 30% by weight; and an effective amount of a thickening agent added is from 0.1% to 25% by weight, calculated in each case on the total composition. An effective amount of the direct dye or the oxidation dyestuffs combinations in such preparations is from 0.1% to 5% by weight, for each, preferably 0.1% to 2%, based upon the total composition, for each, depending on the purpose for which the agent is to be used. An effective amount of an oil replacement agent is from 0.1% to 5% by weight, and an effective amount of a perfume oil is from 0.1% to 5% by weight. An effective amount of reagents for pH adjustment such as ammonia is from 0.1% to 10% preferably from 2% to 5% by weight.

Generally speaking the preparation for bleaching and coloring of the hair contains keratose, an oxidizing agent and the balance up to 100% by weight of one or more of these ingredients, as well as water, and mixtures thereof.

Specific examples of the above ingredients are as follows: higher fatty alcohols having oil replacement properties include fatty alcohols having chain lengths of $C_{12}$ to $C_{14}$ and $C_{16}$ to $C_{18}$; anionic wetting agents include fatty alcohol sulfates having a chain length of $C_{16}$ to $C_{18}$; and nonionic wetting agents include adducts of stearyl alcohol with 8 mols of ethylene oxide.

The application of the bleaching and coloring preparations may be effected at temperatures between 15°C and 40°C, preferably room temperature, in weakly acid, neutral or preferably alkaline medium especially of pH from 8 to 12.

The following examples are merely illustrative of the present invention without being deemed limitative in any manner thereof.

EXAMPLE 1

The keratose required for the following experiments was produced in the following manner:

100 gm of poodle hair was de-oiled by boiling for 1 hour under reflux with methylene chloride, drained off and dried. The dried hair was bleached by means of 2000 gm of 6% hydrogen peroxide solution with the addition of 1% of a 25% ammonia solution, then washed and dried in a vacuum drying cabinet. The dried, bleached hair was treated for 1 hour at a temperature of 60° to 70°C with 2000 gm of a 0.1 N sodium hydroxide solution. After the hair had been filtered off, the dark brown filtrate was dehydrated, leaving dark brown syrupy keratose, which analyzed to contain 6.09% sulfur.

EXAMPLE 2

The bleaching tests on untreated human hair were carried out in the following manner both with and without the addition of keratose prepared in the manner described above in Example 1. For the manufacture of the blonding cream, 8 parts by weight of fatty alcohols having the chain lengths $C_{16}$ to $C_{18}$, 7 parts by weight of fatty alcohol sulfates having the chain length $C_{16}$ to $C_{18}$ and 1 part by weight of fatty alcohols having the chain length $C_{12}$ to $C_{14}$ were melted together by heating at 80°C, and emulsified with 34 parts by weight of water at the same temperature.

The cream obtained after cooling was adjusted with 4 parts by weight of concentrated ammonia solution to pH 10.0, and enough water was added to bring the total up to 100 parts by weight. For the blonding process 100 gm of the cream thus produced was mixed intimately with 28 gm of melamine perhydrate and 7 gm of the keratose produced in the manner described in Example 1, and spread evenly over the hair. After a reaction time of 45 minutes the hair was rinsed in the usual manner and dried. This bleaching process was performed a total of nine times in succession.

For the purposes of comparison, untreated human hair was treated nine times with a bleaching cream of the same composition, but without the addition of keratose.

Examination of the bleached hair led to the following results:

a. Appearance

When wet, the hair which had been treated with the bleaching cream without the addition of kerotose could be stretched like rubber. When pressed together the hairs matted with each other.

When wet, the hair treated with the bleaching cream with keratose added was far less elastic. When pressed together no matting was observed.

b. Texture

The hair bleached without added keratose was hard to the touch, both longitudinally and also in a cross direction. The strands of hair bleached with keratose added were far softer to the touch.

c. Alkali solubility

The determination of the alkali solubility was effected in the manner and described by Erlemann et al in the Journal Soc. Cosmetic Chemists 23, (1972), page 794. In the course thereof the following mean values were obtained from several determinations:

In the case of hair bleached without added keratose, the mean value for alkali solubility was 54.7%.

In the case of the hair bleached with added keratose the mean value of the alkali solubility was substantially lower, being only 46.7%.

d. Damage to hair

Greater damage to the cuticular layer of the hair bleached without the addition of keratose as compared with the hair bleached with the addition of keratose could be seen from a scanner electron microscope.

e. Determination of resistance to splitting

The determination of the resistance to splitting, and also the 15% elongation, was effected at 65% relative humidity of the air and at 20°C in accordance with DIN 53802 by means of an extensometer of Zwick & Co. (DIN is the abbreviation for Deutsche Industrie-Norm representing a series of standard German published test procedures.)

20 hairs with an extended length of 50 mm were stretched until breaking occurred. The run-off speed of the extensometer was 60 mm per minute, the advance of the diagram paper being 5:1. The 15% elongation value indicated the force in pond which was required to stretch the hair having the initial length ($\bar{x}$) of 50 mm to a length of 57.5 mm. The breaking strength represented the force which was required to break the hair.

1. Untreated grey hair

Breaking strength = 79.35 pond, the % elongation at tear as % $\bar{x}$ = 43.9

, 15% elongations = 47.55 pond.

2. Grey hair subjected to the blonding process 9 times without the addition of keratose Breaking strength = 71.35 pond, the % elongation at tear as %$\bar{x}$ = 50.9

15% elongation = 42.5.

3. Grey hair subjected to the blonding process nine times with the addition of keratose Breaking strength = 80.35 pond, the % elongation at tear as %$\bar{x}$ = 50.8

15% elongation = 46.75 pond

The test results set forth above indicate that the values for breaking strength and 15% elongation do not differ substantially in the case of untreated hair, as compared with hair which had been bleached with keratose added. On the other hand, the values for breaking strength and 15% elongation for the hair bleached without the addition of keratose clearly indicate damage to the hair.

EXAMPLE 3

A 6% hydrogen peroxide solution was used as the blonding solution, and shortly before use, was adjusted to a pH value of 10 with ammonia. 95 ml of this solution was intimately mixed with 5 gm of keratose and used, in comparison with a solution without added keratose, for bleaching untreated grey hair. After a treatment time of 2 hours followed by washing and drying in the normal manner, the hair bleached with the addition of keratose still displayed a good shine and texture and showed no tendency to mat. On the other hand, the hair bleached without the addition of keratose was dull, hard in texture, brittle and matted easily.

EXAMPLE 4

For the oxidative coloring of untreated grey hair, 100 gm of coloring cream, based on the known oxidation coloring dyestuffs, containing 0.07 gm p-toluylenediamine-sulphate, 0.01 gm chlororesorcin and 0.01 gm resorcin was intimately mixed shortly before use with 30 gm of 6% solution of hydrogen peroxide and 6 gm of keratose. The hair colored with this coloring cream had a bright shine and was soft and pleasant in texture.

EXAMPLE 5

For the manufacture of a blonding paste, 30 parts by weight of the addition product of 1 mol of stearyl alcohol with 8 mols of ethylene oxide, was mixed intimately with 20 parts by weight of paraffin oil, 10 parts by weight of glycerin, 4 parts by weight of concentrated ammonia solution and 36 parts by weight of water. 100 gm of this highly viscous paste was mixed with 5 gm of sodium perborate and 8 gm of keratose and used for bleaching untreated grey hair. The bleached hair had a bright shine, good elasticity, did not display any influencing of the hair ends and had a pleasant and soft texture.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

I claim:

1. A preparation for the bleaching of hair consisting essentially of:
   A. 0.05% to 10% by weight of keratose,
   B. 3% to 10% by weight of at least one oxidizing agent for liberating active oxygen, calculated as hydrogen peroxide, and
   C. the balance being an ingredient selected from the group consisting of a wetting agent, a thickening agent, a pH adjustment reagent, water, and mixtures thereof 2. The preparation of claim 1, wherein the weight of said keratose is 3% to 7% of the weight of said preparation.

3. The preparation of claim 1, wherein said oxidizing agent is hydrogen peroxide.

4. The preparation of claim 1 wherein said oxidizing agent is selected from the group consisting of hydrogen peroxide, percarbamide, an alkali metal perborate, an alkali metal percarbonate, melamine perhydrate, an alkali metal persulfate and mixtures thereof.

5. In a process for bleaching hair which comprises applying a bleaching agent containing an oxidizing agent to the hair at a temperature and for a time effective to bleach said hair, and removing said agent from the hair; the improvement which consists essentially in utilizing from 0.05% to 10% by weight of keratose in said bleaching agent containing an oxidizing agent.

6. A process for the bleaching of human hair consisting essentially of applying to said hair at a temperature ranging from about 15°C to 40°C for a time sufficient to bleach said hair, an effective amount of the preparation according to claim 1.

7. The process of claim 6, wherein the weight of keratose is 3% to 7% of the weight of said preparation.

8. The process of claim 6 wherein said oxidizing agent is hydrogen peroxide.

9. The process of claim 6 wherein said oxidizing agent is selected from the group consisting of hydrogen peroxide, percarbamide, an alkali metal perborate, an alkali metal percarbonate, melamine perhydrate, an alkali metal persulfate, and mixtures thereof.

* * * * *